United States Patent [19]

Dykstra et al.

[11] Patent Number: 5,643,935

[45] Date of Patent: Jul. 1, 1997

[54] METHOD OF COMBATTING INFECTIOUS DISEASES USING DICATIONIC BIS-BENZIMIDAZOLES

[75] Inventors: Christine C. Dykstra, Chapel Hill; John Perfect, Durham, both of N.C.; David W. Boykin; W. David Wilson, both of Atlanta, Ga.; Richard R. Tidwell, Pittsboro, N.C.

[73] Assignees: The University of North Carolina at Chapel Hill, Chapel Hill; Duke University, Durham, both of N.C.; Georgia State University Research Foundation, Inc., Atlanta, Ga.

[21] Appl. No.: 472,996

[22] Filed: Jun. 7, 1995

[51] Int. Cl.[6] .................................................. A61K 31/505
[52] U.S. Cl. .................................................. 514/394; 514/256
[58] Field of Search .................................. 514/394, 256

[56] References Cited

U.S. PATENT DOCUMENTS

| 4,156,778 | 5/1979 | Rosner et al. | 544/296 |
| 4,933,347 | 6/1990 | Tidwell et al. | 514/256 |
| 4,963,589 | 10/1990 | Tidwell et al. | 514/636 |

OTHER PUBLICATIONS

Bell et al, Antimicrobial Agents and Chemotherapy, vol. 37, No. 12, pp. 2668–2673, Dec. 1993.

*Primary Examiner*—Rebecca Cook
*Attorney, Agent, or Firm*—Bell, Seltzer, Park & Gibson

[57] ABSTRACT

The present invention provides methods for treating *Cryptococcus neoformans* and *Candida albicans* in a subject in need of such treatment. The methods comprises administering to the subject a dicationic bis-benzimidazole in an amount effective to treat the conditions.

9 Claims, No Drawings

METHOD OF COMBATTING INFECTIOUS DISEASES USING DICATIONIC BIS-BENZIMIDAZOLES

The present invention was made with Government support under Grant Number 1U01-AI3363 from the National Institutes of Health. The Government has certain rights to this invention.

FIELD OF THE INVENTION

The present invention relates to methods useful in combatting infectious diseases. Specifically, this invention relates to methods of combatting infectious diseases using dicationic bis-benzimidazole compounds.

BACKGROUND OF THE INVENTION

The need for new antifungal agents has become more pronounced because of the increase in the number of fungal infections which occur in patients who are immunocompromised. There is an increased incidence of fungal infections attributed, for example, to the aggressive use of cancer chemotherapy, organ transplantation, and opportunistic infections associated with acquired immunodeficiency syndrome (AIDS) patients. Fungal infections are among the most common complications of AIDS, as well as of cancer chemotherapy. The major opportunistic fungal pathogens causing disseminated mycoses in immunocompromised hosts include Candida and Cryptococcus.

Currently used antifungal agents for the treatment of systemic mycoses can be classified as polyene antibiotics, including Amphotericin B, flucytosine and synthetic azoles. There can, however, be significant drawbacks to the use of these agents, including limited efficacy and/or toxicity. Accordingly, it is an object of the present invention to provide new compounds useful in the treatment of fungal infections.

SUMMARY OF THE INVENTION

As a first aspect, the present invention provides a method of treating *Cryptococcus neoformans* in a patient in need of such treatment. The method comprises administering to a patient in need of such treatment an amount effective to treat *C. neoformans* of a compound of Formula I:

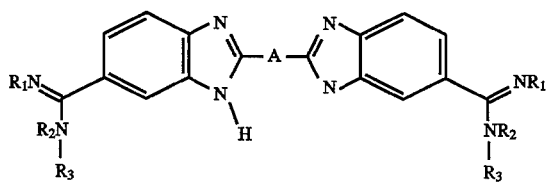

(I)

wherein:

$R_1$ and $R_2$ are each independently selected from the group consisting of H, lower alkyl, alkoxyalkyl, cycloalkyl, aryl, alkylaryl, hydroxyalkyl, aminoalkyl, or alkylaminoalkyl, or $R_1$ and $R_2$ together represent a $C_2$ to $C_{10}$ alkyl, hydroxyalkyl, or alkylene or $R_1$ and $R_2$ together are:

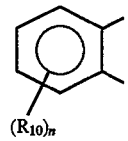

wherein n is a number from 1 to 3, and $R_{10}$ is H or —$CONHR_{11}NR_{15}R_{16}$ wherein $C_{11}$ is lower alkyl and $R_{15}$ and $R_{16}$ are each independently selected from the group consisting of H and lower alkyl; and $R_3$ is H, hydroxy, lower alkyl, cycloalkyl, aryl, alkylaryl, alkoxyalkyl, hydroxycycloalkyl, alkoxycycloalkoxy, hydroxyalkyl, aminoalkyl or alkylaminoalkyl;

A is a heterocyclic aromatic group selected from the group consisting of:

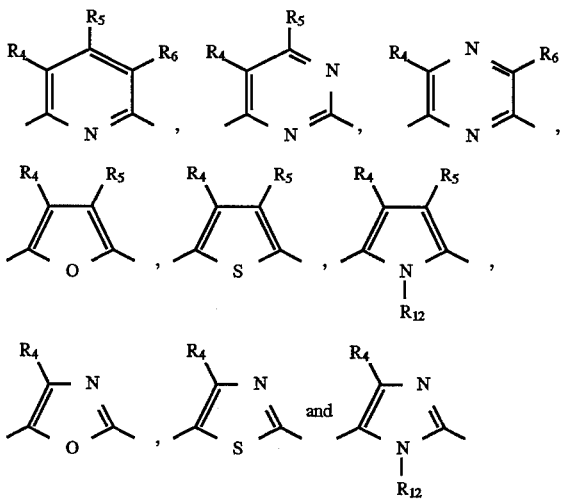

wherein $R_4$, $R_5$, and $R_6$ are each independently selected from the group consisting of H, lower alkyl, halogen, aryl, arylalkyl, aminoalkyl, aminoaryl, oxyalkyl, oxyaryl, or oxyarylalkyl;

$R_{12}$ is hydrogen, lower alkyl, hydroxy, aminoalkyl or alkylaminoalkyl, or a physiologically acceptable salt thereof.

In a preferred embodiment of the invention, $R_1$ and $R_2$ together represent a $C_2$ to $C_4$ alkylene, and $R_3$, $R_4$, $R_5$ and $R_6$ are H and $R_{12}$ is H or lower alkyl. In one aspect of this embodiment of the invention, $R_1$ and $R_2$ together represent

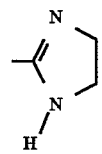

and $R_3$ is H.

In another aspect of this embodiment of the invention, $R_1$ and $R_2$ together represent

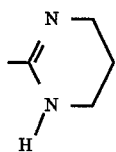

and $R_3$ is H.

In yet another preferred embodiment of the invention, each of $R_1$, $R_2$, $R_3$, $R_4$, $R_5$ and $R_6$ are H and $R_{12}$ is H or lower alkyl.

In yet another preferred embodiment of the invention, each of $R_1$, $R_3$, $R_4$, $R_5$ and $R_6$ are H, $R_2$ is lower alkyl, preferably isopropyl, and $R_{12}$ is H or lower alkyl.

In yet another preferred embodiment of the invention, A is:

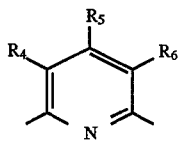

wherein $R_4$, $R_5$, and $R_6$ are each H.

In another preferred embodiment of the invention, A is:

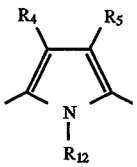

wherein $R_4$ and $R_5$ are each H and $R_{12}$ is H or lower alkyl.

In yet another preferred embodiment of the invention, A is:

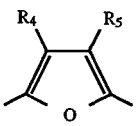

wherein $R_4$ and $R_5$ are each H.

As a second aspect, the present invention provides a method of treating *Candida albicans* in a patient in need of such treatment. The method comprises administering to a patient in need of such treatment a compound of Formula I above in an amount effective to treat *C. albicans*.

As a third aspect, the present invention also provides a method of treating a tumor bearing patient in need of such treatment. The method comprises administering to a patient in need of such treatment a compound of Formula I above in a therapeutically effective amount.

As a fourth aspect, the present invention provides compounds useful for the treatment of *C. neoformans*. The compounds have the structural Formula (I), described above. Currently preferred compounds of Formula I include, but are not limited to, 2,5-bis(5-amidino-2-benzimidazolyl) pyrrole; 2,5-bis-[5-(2-imidazolinyl)-2-benzimidazolyl] pyrrole; 2,6-bis[5-(2-imidazolinyl)-2-benzimidazolyl]pyridine; 1-methyl-2,5-bis(5-amidino-2-benzimidazolyl)pyrrole; 1-methyl-2,5-bis[5-(2-imidazolyl)-2-benzimidazolyl] pyrrole; 1-methyl-2,5-bis[5-(1,4,5,6-tetrahydro-2-pyrimidinyl)-2-benzimidazolyl] pyrrole; 2,6-bis(5-amidino-2-benzimidazoyl)pyridine; 2,6-bis[5-(1,4,5,6-tetrahydro-2-pyrimidinyl)-2-benzimidazolyl] pyridine; 2,5-bis(5-amidino-2-benzimidazolyl)furan; 2,5-bis[5-(2-imidazolinyl)-2-benzimidazolyl]furan; 2,5-bis(5-N-isopropylamidino-2-benzimidazolyl)furan; and physiologically acceptable salts thereof. Novel compounds useful for treating *C. albicans* and for combatting tumors are also disclosed.

The foregoing and other objects and aspects of the present invention are explained in detail in the specification set forth hereinbelow.

DETAILED DESCRIPTION OF THE INVENTION

As used herein, the term "lower alkyl," refers to C1 to C6 linear or branched alkyl, such as methyl, ethyl, propyl, butyl, isopropyl, sec-butyl, tert-butyl, butyl, pentyl, isopentyl, and hexyl. The term "cycloalkyl" as used herein refers to C3 to C6 cyclic alkyl, such as cyclopropyl, cyclobutyl, cyclopentyl, and cyclohexyl. The term "aryl" as used herein refers to C3 to C10 cyclic aromatic groups such as phenyl, naphthyl, and the like, and includes substituted aryl groups such as tolyl. The term "hydroxyalkyl" as used herein refers to C1 to C4 linear or branched hydroxy-substituted alkyl, i.e., —$CH_2OH$, —$(CH_2)_2OH$, etc. The term "aminoalkyl" as used herein refers to C1 to $C_4$ linear or branched amino-substituted alkyl, wherein the term "amino" refers to the group NR'R", wherein R' and R" are independently selected from H or lower alkyl as defined above, i.e., —$NH_2$, —$NHCH_3$, —$N(CH_3)_2$, etc. The term "alkoxyalkyl" as used herein refers to C1 to C6 linear or branched alkoxy, such as methoxy, ethoxy, propyloxy, butyloxy, isopropyloxy, and t-butyloxy.

As noted above, the methods of the present invention are useful for treating *Cryptococcus neoformans*. The methods of the present invention are useful for treating these conditions in that they inhibit the onset, growth, or spread of the condition, cause regression of the condition, cure the condition, or otherwise improve the general well-being of a subject inflicted with, or at risk of contracting the condition.

Subjects to be treated by the methods of the present invention are typically human subjects although the methods of the present invention may be useful with any suitable subject known to those skilled in the art.

As noted above, the present invention provides pharmaceutical formulations comprising the aforementioned compounds of Formula I, or pharmaceutically acceptable salts thereof, in pharmaceutically acceptable carriers for aerosol, oral, and parenteral administration as discussed in greater detail below. Also, the present invention provides such new compounds or salts thereof which have been lyophilized and which may be reconstituted to form pharmaceutically acceptable formulations for administration, as by intravenous or intramuscular injection.

The therapeutically effective dosage of any specific compound, the use of which is in the scope of present invention, will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration. The duration of the treatment is usually once per day for a period of two to three weeks or until the *Cryptococcus neoformans* infection is essentially controlled. Lower doses given less frequently can be used to prevent or reduce the incidence of recurrence of the infection.

In accordance with the present method, a compound of Formula I, or a pharmaceutically acceptable salt thereof, may be administered orally or through inhalation as a solid, or may be administered intramuscularly or intravenously as a solution, suspension, or emulsion. Alternatively, the compound or salt may also be administered by inhalation, intravenously or intramuscularly as a liposomal suspension. When administered through inhalation the compound or salt should be in the form of a plurality of solid particles or droplets having a particle size from about 0.5 to about 5 microns, preferably from about 1 to about 2 microns.

Besides providing a method for treating *Cryptococcus neoformans*, the compounds of Formula I also provide a method for prophylaxis against *Cryptococcus neoformans* in an immunocompromised patient, such as one suffering from AIDS, who has had at least one episode of *Cryptococcus neoformans* but who at the time of treatment is not exhibiting signs of infection. As *Cryptococcus neoformans* is an especially potentially devastating disease for immunocompromised patients it is preferable to avoid the onset of *Cryptococcus neoformans* as compared to treating the disease after it has become symptomatic. Accordingly, the present invention provides a method for the prophylaxis against *Cryptococcus neoformans* comprising administering to the patient a prophylactically effective amount of a compound of Formula I or a pharmaceutically acceptable salt thereof. The forms for administration of the compound or salt in accordance with this method may be the same as utilized for the purpose of actually treating a patient suffering from *Cryptococcus neoformans* infection.

An additional useful aspect of the present invention is a method for prophylaxis against even an initial episode of *Cryptococcus neoformans* infection in an immunocompromised patient who has never experienced an episode of *Cryptococcus neoformans* infection. In this respect, a patient who has been diagnosed as being immunocompromised, such as one suffering from AIDS or ARC (AIDS related complex), even before the onset of an initial episode of *Cryptococcus neoformans* infection may avoid or delay suffering from the infection by having administered a prophylactically effective amount of a compound of Formula I or a pharmaceutically acceptable salt thereof. The compound or salt may be administered in the same fashion as in the treatment of patients suffering from *Cryptococcus neoformans* infection.

The present invention also provides new pharmaceutical compositions suitable for intravenous or intramuscular injection. The pharmaceutical compositions comprise a compound of Formula I, or a pharmaceutically acceptable salt thereof, in any pharmaceutically acceptable carrier. If a solution is desired, water is the carrier of choice with respect to water-soluble compounds or salts. With respect to the water-insoluble compounds or salts, an organic vehicle, such as glycerol, propylene glycol, polyethylene glycol, or mixtures thereof, may be suitable. In the latter instance, the organic vehicle may contain a substantial amount of water. The solution in either instance may then be sterilized in any suitable manner, preferably by filtration through a 0.22 micron filter. Subsequent to sterilization, the solution may be filled into appropriate receptacles, such as depyrogenated glass vials. Of course, the filling should be done by an aseptic method. Sterilized closures may then be placed on the vials and, if desired, the vial contents may be lyophilized.

In addition to compounds of Formula I or their salts, the pharmaceutical compositions may contain other additives, such as pH adjusting additives. In particular, useful pH adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In yet another aspect of the present invention, there is provided an injectable, stable, sterile composition comprising a compound of Formula I, or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into man. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Other pharmaceutical compositions may be prepared from the water-insoluble compounds of Formula I, or salts thereof, such as aqueous base emulsions. In such an instance, the composition will contain a sufficient amount of pharmaceutically acceptable emulsifying agent to emulsify the desired amount of the compound of Formula I or salt thereof. Particularly useful emulsifying agents include phosphatidyl cholines, and lecithin.

Further, the present invention provides liposomal formulations of the compounds of Formula I and salts thereof. The technology for forming liposomal suspensions is well known in the art. When the compound of Formula I or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds of Formula I or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation.

These formulations comprise a solution or suspension of the desired compound of Formula I or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the solid compound of Formula I, or a salt thereof, in any appropriate manner known in the art, such as by micronization. Most preferably, the size of the solid particles or droplets will be from about 1 to about 2 microns. In this respect, commercial nebulizers are available to achieve this purpose.

Preferably, when the pharmaceutical formulation suitable for administration as an aerosol is in the form of a liquid, the formulation will comprise a water-soluble compound of Formula I or a salt thereof, in a carrier which comprises water. A surfactant may be present which lowers the surface tension of the formulation sufficiently to result in the formation of droplets within the desired size range when subjected to nebulization.

As indicated, the present invention provides both water-soluble and water-insoluble compounds and salts. As used in the present specification, the term "water-soluble" is meant to define any composition which is soluble in water in an amount of about 50 mg/mL, or greater. Also, as used in the present specification, the term "water-insoluble" is meant to define any composition which has solubility in water of less than about 20 mg/mL. For certain applications, water soluble compounds or salts may be desirable whereas for other applications water-insoluble compounds or salts likewise may be desirable.

Examples of compounds exemplary of Formula (I) above include, but are not limited to:
2,5-bis(5-amidino-2-benzimidazolyl) pyrrole;
2,5-bis-[5-(2-imidazolinyl)-2-benzimidazolyl] pyrrole;
2,6-bis[5-(2-imidazolinyl)-2-benzimidazolyl]pyridine;
1-methyl-2,5-bis(5-amidino-2-benzimidazolyl)pyrrole;
1-methyl-2,5-bis[5-(2-imidazolyl)-2-benzimidazolyl] pyrrole;
1-methyl-2,5-bis[5-(1,4,5,6-tetrahydro-2-pyrimidinyl)-2-benzimidazolyl] pyrrole;
2,6-bis(5-amidino-2-benzimidazoyl)pyridine;
2,6-bis[5-(1,4,5,6-tetrahydro-2-pyrimidinyl)-2-benzimidazolyl] pyridine;
2,5-bis(5-amidino-2-benzimidazolyl)furan;
2,5-bis[5-(2-imidazolinyl)-2-benzimidazolyl]furan;
2,5-bis(5-N-isopropylamidino-2-benzimidazolyl)furan;
and physiologically acceptable salts thereof.

As indicated, the compounds used in the present invention may be present as pharmaceutically acceptable salts. Such salts include the gluconate, lactate, acetate, tartarate, citrate, phosphate, borate, nitrate, sulfate, and hydrochloride salts.

Methods of combating *Candida albicans* with the compounds of Formula I above are carried out in essentially the same manner as given above, and pharmaceutical formulations of the compounds of Formula I for combating *Candida albicans* are prepared in essentially the same manner as given above.

The compounds of Formula (I) also show pharmaceutical activity in combatting cancer cells in vitro and may be useful in combatting corresponding tumors in vivo. For example, the compounds of Formula (I) show cytotoxic activity against leukemia cells. Accordingly, the present invention also includes a method of treating a tumor bearing patient in need of such treatment. The method comprises administering to the patient a compound of Formula (I) in an amount effective to combat the tumor. Methods of combating tumors with the compounds of Formula I above are carried out in essentially the same manner as given above, and pharmaceutical formulations of the compounds of Formula I for combating tumors are prepared in essentially the same manner as given above.

Further, it is anticipated that the antineoplastic efficacy of the compounds of Formula (I) can be improved or supplemented by the cojoint administration of these compounds with other known antineoplastic agents, as, for example, in a combination chemotherapy regimen. Exemplary of such known antineoplastic agents are, without limitation, vinca alkaloids such as vincristine, vinblastine, and vindesine; epipodophyllotoxins such as etoposide and teniposide; anthracycline antibiotics such as daunorubicin, doxorubicin, mitoxantraone, and bisanthrene; actinomycin D; and plicamycin.

The compounds of the present invention may be prepared according to methods known in the art, particularly in light of the disclosure and examples set forth below. According to one method, the compounds of Formula I can be prepared by condensation of an appropriate heterocyclic compound (i.e., pyrrole, pyridine, furan, etc.) dicarboxaldehyde (for example pyrrole-2,5-dicarboxaldehyde) which can be prepared according to the teaching of T. Cresp, et al., *J.Chem. Soc. Perkins Tran.* 1, 2961 (1973) with the appropriate diaminophenyl compound (for example diaminobenzamidine prepared according to T. Fairley, et al., *Med.Chem.* 36, 1746 (1993). The condensation reaction can be conducted according to the method of S. Kumar, et al., *Indian J.Chem* 20B, 254 (1981).

The diaminophenyl compounds can be prepared, for example, by reduction of nitro groups of 3,4-dinitrobromobenzene to form 3,4-diaminobromobenzene. Nitrilization of this compound to the corresponding 3,4-diaminonitrilebenzene can be conducted by reacting copper (I) cyanide with the thus prepared 3,4-dinitrobromobenzene in refluxing DMF according to the standard techniques. See, J. Spychala, et al., *European J. Med. Chem.* 29: 363 (1994). The nitrile can then be converted to the imidate ester by the Pinner methodology, according to B. Das, et al., *J. Med. Chem.* 20, 1219 (1977). The imidate ester can be converted into the compounds of Formula (I), for example, by reaction with ammonium or the appropriate aminoalkane or diaminoalkane (such as ethylenediamine, propylenediamine, etc.), to form an amidino group, an imidazolinyl group, an 1,4,5, 6-tetrahydro-2-pyrimidinyl group, respectively. The bis-nitrile can also be converted to the bis-dicationic compound by fusion of the nitrile directly with the hydrochloride salt of the appropriate diamine by thermolysis. This technique is particularly useful for the preparation of compounds wherein the $R_1$ and $R_2$ groups together form a cyclic alkyl.

The compounds of Formula I above can also be prepared by first preparing an appropriate intermediate, such as 2,5-bis(5-bromo-2-benzimidazolyl)pyrrole by the base promoted condensation, for example, of 1-bromo-3,4-diaminobenzene and pyrrole-2,5-dicarboxaldehyde, according to the method of S. Kumar, et al., supra. The intermediate can then be obtained by nitrilization followed by imidate ester formation and conversion into the corresponding amidino as described above.

The salts of the present invention may be prepared, in general, by reacting two equivalents of the heterocyclic base compound with the desired acid in solution. After the reaction is complete, the salts are crystallized from solution by the addition of an appropriate amount of solvent in which the salt is insoluble.

The compounds of the present invention are useful not only in methods for treating *Cryptococcus neoformans* and *Candida albicans* but also in methods of inhibiting enzymes such as topoisomerase. The compounds of Formula (I) are particularly useful for inhibiting topoisomerase II. See, S. Doucc-Racy, et al., *Proc. Natl. Acad. Sci. USA* 83: 7152 (1986).

The present invention will be further illustrated by the following non-limiting examples, in which "g" means grams, "mg" means milligrams, "μg" means micrograms, "mmol" means millimoles, "h" means hours, "ml" means milliliter, "M" means molar, "mM" means millimolar, "μM" means micromolar, "UV" means ultraviolet, "HCl" means hydrogen chloride, "mp" means melting point, "HCN" means hydrocyanic acid and "°C." means degrees Celsius.

For the following examples melting points were recorded using a Thomas Hoover (Uni-Melt) capillary melting point apparatus and are uncorrected. $^1$H NMR and $^{13}$C NMR spectra were recorded employing a Varian GX400 spectrometer and chemical shifts (d) are in ppm relative to TMS unless otherwise noted. Mass spectra were recorded on a VG Instruments 70-SE spectrometer (Georgia Institute of Technology, Atlanta, Ga.). IR spectra were recorded using a Michelson 100 (Bomem, Inc.) instrument. Elemental analysis were obtained from Atlantic Microlab Inc. (Norcross, Ga.) and are within +0.4 of the theoretical values. All chemicals and solvents were purchased from Aldrich Chemical Co. or Fisher Scientific.

In the Examples below, the following compound designations are used throughout.

saturated ethanol. After standing overnight in the refrigerator, the green solid was collected by filtration, washed with anhydrous ether and dried under vacuum to yield 0.5 g (76%) yield of solid. mp>300° C. $^1$HNMR (DMSO-$d_6$) (7.54 (s, 2H, pyrrole), 7.80 (dd, J=8.8 and 0.8 Hz, Ar—H, 2H), 7.87 (d, J=8.4 Hz, 2H, Ar—H), 8.25 (s, 2H, Ar—H), 9.18, 9.48 (brs, brs, NH). Anal. ($C_{20}N_{17}N_9 \cdot 3HCl \cdot 3H_2O$) C,H,N. MS: m/e 384 (M+1).

EXAMPLE 2

Preparation of 2,5-bis-[5-(2-imidazolinyl)-2-benzimidazolyl] pyrrole 2,5-bis-[5-(2-imidazolinyl)-2-benzimidazolyl] pyrrole (Compound 2). A protocol similar to that used in Example 1 above was used for the condensation of pyrrole-2,5-dicarboxaldehyde and 2-(3,4-diaminophenyl) imidazoline to give a 86% yield of solid. mp>300° C. $^1$HNMR (DMSO-$d_6$) (4.04 (s, 8H, NCH$_2$CH$_2$N), 7.39 (s, 2H, pyrrole), 7.86 (d, J=8.8 Hz, 2H, Ar—H), 7.92 (dd, J=8.4 and 1.6 Hz, 2H, Ar—H), 8.44 (s, 2H, Ar—H), 10.71 (s, NH). Anal. ($C_{24}H_{21}N_9 \cdot 3HCl \cdot 4H_2O$) C,H,N. MS: m/e 436 (M+1).

EXAMPLE 3

Preparation of 2,6-bis[5-(2-imidazolinyl)-2-benzimidazolyl] pyridine 2,6-bis[5-(2-imidazolinyl)-2-benzimidazolyl]pyridine (Compound 3). A protocol similar to that used in Examples 1 and 2 above was used for condensation of 2,6-pyridine carboxyaldehyde and 2-(3,4-diaminophenyl)imidazoline to give an 85% yield of solid. mp>300° C. $^1$HNMR (DMSO-

| Compound # | Name |
|---|---|
| 1 | 2,5-bis(5-amidino-2-benzimidazolyl)pyrrole |
| 2 | 2,5-bis-[5-(2-imidazolinyl)-2-benzimidazolyl]pyrrole |
| 3 | 2,6-bis[5-(2-imidazolinyl)-2-benzimidazolyl]pyridine |
| 4 | 1-Methyl-2,5-bis(5-amidino-2-benzimidazolyl)pyrrole |
| 5 | 1-methyl-2,5-bis[5-(2-imidazolinyl)-2-benzimidazolyl]pyrrole |
| 6 | 1-Methyl-2,5-bis[5-(1,4,5,6-tetrahydro-2-pyrimidinyl)-2-benzimidazolyl]pyrrole |
| 7 | 2,6-bis(5-amidino-2-benzimidazoyl)pyridine |
| 8 | 2,6-bis[5-(1,4,5,6-tetrahydro-2-pyrimidinyl)-2-benzimidazolyl]pyridine |
| 9 | 2,5-bis(5-amidino-2-benzimidazolyl)furan |
| 10 | 2,5-bis[5-(2-imidazolinyl)-2-benzimidazolyl]furan |
| 11 | 2,5-bis(5-N-isopropylamidino-2-benzimidazolyl)furan |

EXAMPLE 1

Preparation of 2,5-bis(5-amidino-2-benzimidazolyl) pyrrole 2,5-bis(5-amidino-2-benzimidazolyl) pyrrole (Compound 1). A solution of pyrrole-2,5-dicarboxaldehyde (Cresp, T., Sargent, M., *J.Chem.Soc. Perkin Trans.* 1, 2961 (1973)) (0.25 g, 2 mmol), 3,4-diaminobenzamidine (Fairley TA, Tidwell RR, Donkor I, Naiman NA, Ohemeng KA, Bentley A and Cory M. J., *Med.Chem.* 36, 1746 (1993)) (0.6 g, 4 mmol) and 1,4-benzoquinone (0.432 g, 4 mmol) in ethanol (40 ml) was heated at reflux for 4 hours (under nitrogen) (Kumar, S., Konsal, V., Bhaduri, A., *Indian J.Chem.* 20B, 254 (1981). The reaction mixture was cooled to room temperature and the dark solid was collected by filtration, washed with cold ethanol, anhydrous ether and dried to yield 0.45 g (59%) of the free base. This solid was dissolved slowly in hot ethanol (300 ml) and filtered. The filtrate volume was reduced to 70 ml and acidified with HCl- $d_6$) (4.05 (s, 8H, N—CH$_2$CH$_2$N), 7.96 (m, 4H, Ar—H), 8.30 (t, 1H, pyridine), 8.49–8.51 (m, 4H, Ar—H), 10.71 (s, NH). Anal. ($C_{25}H_{21}N_9 \cdot 3HCl \cdot 3H_2O$) C,H,N. MS: m/e 448 (M+1).

EXAMPLE 4

Preparation of 1-Methyl-2,5-bis(5-amidino-2-benzimidazolyl)pyrrole

1-Methyl-2,5-bis(5-amidino-2-benzimidazolyl)pyrrole (Compound 4). A protocol similar to that described above in Examples 1–3 was employed for the condensation of 3,4-diaminobenzamidine (Fairley TA, Tidwell RR, Donkor I, Naiman NA, Ohemeng KA, Bentley A and Cory M. J., *Med. Chem.* 36, 1746 (1993) ) with 1-methylpyrrole-2,-5-dicarboxaldehyde to yield 0.48 g (46%) of product. mp>300° C.; $^1$HNMR (DMSO-$d_6$) (4.72 (s, 3H, CH$_3$—N), 7.33 (s, 2H, pyrrole), 7.73 (dd, J=8 and 1.2 Hz, 2H, Ar—H), 7.80 (d, J=8.4 Hz, Ar—H), 8.19 (s, 2H, Ar—H) 9.11, 9.38 (brs, brs, NH-amidine). Anal. ($C_{21}H_{19}N_9 \cdot 3HCl \cdot H_2O$) C,H, N. MS: m/e 398 (M+1).

EXAMPLE 5

Preparation of 1-methyl-2,5-bis[5-(2-imidazolyl)-2-benzimidazolyl] pyrrole 1-methyl-2,5-bis[5-(2-imidazolyl)-2-benzimidazolyl] pyrrole (Compound 5). A protocol similar to that described above in Examples 1–4 was employed for the condensation of 2-(3,4-diaminophenyl)-imidazoline with 1-methylpyrrole-2,-5 - dicarboxaldehyde. A yield of 83% of solid, mp>300° C., was obtained. $^1$HNMR (4.04 (s, 8H, NCH$_2$CH$_2$N), 4.72 (s, 3H, CH$_3$N), 7.30 (s, 2H, pyrrole), 7.84 (qAB, J=8.4 and 8 Hz, 4H, Ar—H), 8.36 (s, 2H, Ar—H), 10.60 (s, NH). Anal. (C$_{25}$H$_{23}$N$_9$.3HCl.3H$_2$O) C,H, N. MS: m/e 450 (M+1).

EXAMPLE 6

Preparation of 1-Methyl-2,5-bis[5-(1,4,5,6-tetrahydro-2-pyrimidinyl)-2-benzimidazolyl] pyrrole 1-Methyl-2,5-bis[5-(1,4,5,6-tetrahydro-2-pyrimidinyl)-2-benzimidazolyl] pyrrole (Compound 6). A protocol similar to that described above for Examples 1–5 was employed for the condensation of 2-(3,4-diaminophenyl) tetrahydropyrimidine with 1-methylpyrrole-2,5-dicarboxaldehyde. A yield of 83% of solid, mp>300° C., was obtained. $^1$HNMR (2.01 (m, 4H, CH$_2$), 3.52 (brs. 8H, CH$_2$N), 4.72 (s, 3H, CH$_3$N), 7.31 (s, 2H, pyrrole), 7.60 (d, J=8.4 Hz, 2H, Ar—H), 7.80 (d, J=8.4 Hz, 2H, AR-H), 8.06 (s, 2H, Ar—H), 9.99 (s, NH). Anal. (C$_{27}$H$_{27}$N$_9$.3HCl.4H$_2$O) C,H,N. MS: m/e 478 (M+1).

EXAMPLE 7

Preparation of 2,6-bis(5-amidino-2-benzimidazoyl) pyridine 2,6-bis(5-amidino-2-benzimidazoyl)pyridine (Compound 7). A protocol similar to that described in Examples 1–6 above was used to condense 2,6-pyridine dicarboxaldehyde with 3,4-diaminobenzamidine to yield 89% of a solid, mp>300° C. $^1$HNMR (DMSO-d$_6$) (7.79 (dd, J=8.4 and 1.6 Hz, 2H, Ar—H), 7.94 (d, J=8.4 Hz, 2H, Ar—H), 8.28–8.34 (m, 3H, Ar—H), pyridine), 8.51 (d, J=8 Hz, 2H, pyridine), 9.12, 9.45 (brs, brs, NH). Anal. (C$_{21}$H$_{17}$N$_9$.3HCl.2H$_2$O) C,H,N. MS: m/e 396 (M+1).

EXAMPLE 8

Preparation of 2,6-bis[5-(1,4,5,6-tetrahydro-2-pyrimidinyl)-2-benzimidazolyl] pyridine 2,6-bis[5-(1,4,5,6-tetrahydro-2-pyrimidinyl)-2-benzimidazolyl] pyridine (Compound 8). A protocol similar to that described above in Examples 1–7 was used to condense 2,6-pyridine dicarboxaldehyde with 2-(3,4-diaminophenyl)tetrahydropyrimidine to give an 89% yield of solid, mp>300° C. $^1$HNMR (DMSO-d$_6$) (2.03 (m, 4H, CH$_2$), 3.54 (brs, 8H, CH$_2$N), 7.66 (d, J=8.4 Hz, 2H, Ar—H), 7.84 (d, J=8.4 Hz, 2H, Ar—H), 8.17 (s, 2H, Ar—H), 8.29 (t, 1H, pyridine), 8.43 (d, J=8 Hz, 2H, pyridine), 10.04 (s, NH). Anal. (C$_{27}$H$_{25}$N$_9$.3HCl.4H$_2$O) C,H,N. MS: m/e 476 (M+1).

EXAMPLE 9

Preparation of 2,5-bis(5-amidino-2-benzimidazolyl) furan 2,5-bis(5-amidino-2-benzimidazolyl] furan. A protocol similar to that described above in Examples 18–25 above was used to condense 2,5-furan dicarboxyaldehyde with 3,4-diaminobenzamidine. A solution of 2,5-furan dicarboxyaldehyde (0.25 g, 2 mmol), 3,4-diaminobenzamidine (0.6 g, 4 mmol) and benzoquinone (0.43 g, 4 mmol) in ethanol (100 mL) was refluxed under nitrogen for 4 hours. After cooling, solvent was reduced and to the residue dry ether was added. The precipitated solid was filtered and washed with dry ether. The yellow-green solid was acidified with concentrated HCl. After standing overnight ether was added and the solid was collected by filtration, washed with dry ether, and dried in vacuum at 90° C. for 48 hours. Yield 0.5 g (52.2%) of the yellow-green powder, mp>300° C. MS (FAB): m/z 385 (M$^+$+1); HRMS: calc. mass (free base): 385.1525 (M$^+$+1); observed mass: 385.1535, $^1$H NMR (DMSO-d$_6$, TMS)δ: 9.30 s, 4H (N—H); 8.95 s, 4H (N—H); 8.19 s, 2H (phenyl); 7.81 d, 2H, J=8.8 Hz; 7.72 d, 2H, J=8.4 Hz; 7.60 s 2H (furan), $^{13}$C NMR (DMSO-d$_6$+D$_2$O)δ: 166.8; 146.3; 146.1; 142.2; 139.7; 123.4; 122.7; 117.1; 116.1; 115.4. Anal. (C$_{20}$H$_{16}$N$_8$O.2HCl.1.5H$_2$O) C,H,N

EXAMPLE 10

Preparation of 2,5-bis[5-(2-imidazolinyl)-2-benzimidazolyl] furan 2,5-bis[5-(2-imidazolinyl)-2-benzimidazolyl] furan. A protocol similar to that described above in Examples 18–26 above was used to condense 2,5-furan dicarboxyaldehyde with 2-(3,4-diaminophenyl) imidazoline. A solution of 2,5-furan dicarboxyaldehyde (0.25 g, 2 mmol), 2-(3,4-diaminophenyl)imidazoline (0.7 g, 4 mmol) and benzoquinone (0.43 g, 4 mmol) in ethanol (100 mL) was refluxed under nitrogen for 4 hours. After cooling, solvent was reduced and to the residue dry ether was added. The precipitated solid was filtered and washed with dry ether. The yellow-green solid was acidified with concentrated HCl. After standing overnight ether was added and solid was collected by filtration, washed with dry ether, and dried in vacuum at 90° C. for 3 days. Yield 0.45 g (38.1%) of the green powder, mp>300° C. MS (FAB): m/z 437 (M$^+$+1); HRMS: calc. mass (free base): 437.1838 (M$^+$+1); observed mass: 437.1832, $^1$H NMR (DMSO-d$_6$, TMS)δ: 10.53 s, 4H (N—H); 8.38 s, 2H; 7.87 d, 2H, J=8.5 Hz; 7.83 d, 2H, J=8.2 Hz; 7.62 s, 2H; 4.04 s, 8H. $^{13}$C NMR (DMSO-d$_6$+D$_2$O, TMS): δ 166.3; 146.2; 146.1; 142.3; 139.8; 123.7; 117.6; 116.9; 116.1; 115.5; 45.0. Anal. (C$_{24}$H$_{20}$N$_8$O.2HCl.5H$_2$O) C,H,N

EXAMPLE 11

Preparation of 2,5-bis(5-N-isopropylamidino-2-benzimidazolyl) furan 2,5-bis(5-N-isopropylamidino-2-benzimidazolyl] furan. A protocol similar to that described above in Examples 18–27 above was used to condense 2,5-furan dicarboxyaldehyde with 3,4-diamino-N-isopropylbenzamidine. A solution of 2,5-furan dicarboxyaldehyde (0.25 g, 2 mmol), 3,4-diamino-N-isopropylbenzamidine (0.77 g, 4 mmol), and benzoquinone (0.43 g, 4 mmol) in ethanol (100 mL) was refluxed under nitrogen for 4 hours. After cooling, solvent was reduced and to the residue dry ether was added. The precipitated solid was filtered and washed with dry ether and dried. After drying the green solid was dissolved in anhydrous ethanol saturated with HCl (50 mL) and heated until boiling started, then allowed to cool. The green solid was collected by filtration, and dried in vacuum at 90° C. for 3 days. Yield 0.67 g (53.6%) of the yellow-green powder, mp>300° C. MS (FAB): m/z 469 (M$^+$+1); HRMS: calc. mass (free base): 469.2464 (M⁺+1); observed mass: 469.2475, $^1$H NMR (DMSO-$d_6$, TMS): δ 9.60+9.58 s+s, 2H (N—H); 9.45 s, 2H (N—H); 9.45 s 2H (N—H); 9.04 s, 2H (N—H); 8.06 s, 2H (phenyl); 7.82 d, 2H, J=8.4 Hz; 7.69 s, 2H (furan); 7.62 d, 2H, J=8.2 Hz; 4.09 m, 2H (CH), J=7.02 Hz; 1.32 d 12H (CH$_3$), J=6.3 Hz; $^{13}$C NMR (DMSO-$d_6$+$D_2O$, TMS): δ 162.8; 145.9; 145.1; 140.9; 138.5; 124.5; 124.0; 116.9; 115.9; 115.9; 45.9; 21.7. Anal. ($C_{26}H_{28}N_8O \cdot 3HCl \cdot 5H_2O$) C,H,N

EXAMPLE 12

Activity of Compounds Against *Cryptococcus neoformans* and *Candida albicans*

The activity of various compounds of Formula I against *Cryptococcus neoformans* and *Candida albicans* is shown in Table 1. Activity of the compounds were assessed using a standard in vitro fungal cell growth inhibition assay (the broth dilution antifungal susceptibility testing of yeast, proposed standard document M27-P, validated by the National Committee for Clinical Laboratory Standards, 1992). Briefly, this broth dilution procedure uses RPMI media, and an inoculum of $10^4$ cells. Control tubes contained media alone. After the minimal inhibitor concentration was determined by the above procedure, tubes with no visible growth were subcultured to determine the minimum fungicidal concentration by using criteria of less than 0.01% survival of original inoculum. Two organisms were tested: (1) H99, a clinical isolate of *C. neoformans* which is fully susceptible to azoles and polyenes in vitro and in vivo; and (2) A39, a clinical isolate of *C. albicans* which is fully susceptible to azoles and polyenes.

The MFC's (minimum fungicidal concentration) against these two important AIDS-associated fungal infections are shown in Table 1. MFCs were determined following the method of McGinnis.

TABLE 1

| | | | MFC (μM) | | IC$_{50}$ (μM) | *C. neoformans* topoisomerase (μM) | | ΔT$_m$ oligo | L1210 Cells |
|---|---|---|---|---|---|---|---|---|---|
| Compound | A | Y | *C. neoformans* | *C. albicans* | *S. cerevisiae* | I | II | binding | IC$_{50}$ (μM) |
| 1 | pyrrole | Am | 2.85 | 5.71 | 45 | 50–100 | >5 | 18.1 | 0.21 |
| 2 | pyrrole | Im | 107 | 26.8 | <1 | >100 | <6.25 | 17.6 | 1.07 |
| 3 | pyridine | Im | 5.2 | 2.6 | 10 | 250–500 | 6.25 | 15.8 | 1.26 |
| 4 | 1-methylpyrrole | Am | 5.69 | 2.84 | 90 | 5–6 | 1–2 | 20.3 | 0.81 |
| 5 | 1-methylpyrrole | Im | 2.54 | 5.09 | >100 | 25–50 | 1.25 | 22.5 | 1.51 |
| 7 | pyridine | Am | >179 | >179 | 95 | 125–250 | <62 | 15.3 | 13.64 |
| 8 | pyridine | THP | 19.02 | >52 | 304 | 250–500 | 50–60 | 14.8 | 3.0 |
| 9 | furan | Am | 1.61 | 6.44 | | | | | |
| 10 | furan | Im | 2.60 | 5.21 | | | | | |

Notes

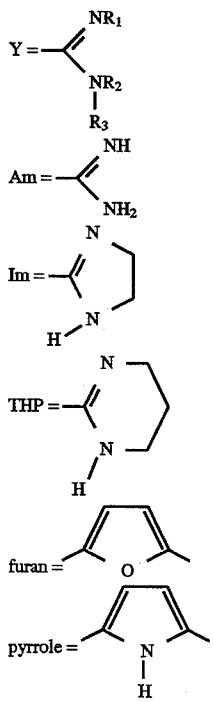

TABLE 1-continued

| Compound A | Y | MFC (µM) C. neoformans | MFC (µM) C. albicans | IC$_{50}$ (µM) S. cerevisiae | C. neoformans topoisomerase (µM) I | C. neoformans topoisomerase (µM) II | ΔT$_m$ oligo binding | L1210 Cells IC$_{50}$ (µM) |
|---|---|---|---|---|---|---|---|---| methyl pyrrole = pyridine =

EXAMPLE 13

Nucleic Acid Binding Measurements

DNA binding potency was determined for each of the compounds because previous work had determined that the binding of dicationic molecules to DNA is a prerequisite for their antimicrobial activity. See e.g., Tidwell, R. R., et al., *Antimicrob. Agents Chemother.* 37, 1713–1716 (1993); Bell, C. A., et al., *Antimicrob. Agents Chemother.* 35, 1099–1107 (1991). The DNA binding of the compounds was determined by the change in melting of the DNA bound to the compounds. The method is well documented and is a considered a standard method for determining DNA binding strength. See Cory, M.. et al., *J. Med. Chem.* 25, 431–438 (1992). In brief, a UV-visible light spectrophotometer with a cuvette changer was interfaced to a microcomputer that recorded the cuvette temperature and DNA-absorbance data at 259 nm as the sample was heated at a rate of 18° C./h. Calf thymus DNA was used at an initial absorbance of 0.3 A$_{259}$. The midpoint of each denaturation curve was determined after graphic selection on the computer of the starting and ending absorbance temperature for each curve of each experiment. DNA or DNA bound to experimental compound was run in each experiment and the ΔT$_m$s were determined from the polynucleotide T$_m$ for that experiment. The greater the change in melting point, the more potent the DNA binding of the molecules. The results are set forth in Table 1 above.

EXAMPLE 14

Anti-tumor Activity

Source: L1210 cells were obtained from the American Type Culture Collection (ATCC#CCL219). This line is a mouse lymphocytic leukemia line first described by E. Law et al., *J. Natl. Cancer Inst.* 10, 179–192 (1949) as a tumor arising in a mouse following skin paintings with 0.2% methycholanthrene. The first report of suspension culture was reported by G. Moore et al. *J. Natl. Cancer Inst.* 36, 405–421 (1966). This line has been used extensively for routine screening programs of chemical agents and natural products for cytotoxic activity and is also utilized in preliminary testing for antitumor activity by the NCI in cancer chemotherapy screening studies.

The in vitro cytotoxicity studies were performed essentially as described by Denizot and Lang, "Rapid colorimetric assay for cell growth and survival: Modification of tetrazolium dye procedure giving improved sensitivity and reliability", *J. Immunological Methods* 89, 271 (1986), but with the following modifications. Since many of the drugs had color interference, the viability of the cells was determined with a $^3$H-thymidine incorporation method. L1210 cells in DMEM+10% fetal calf serum were plated at 2.0×10$^4$ cells/well. An equal volume of test compound was added to each well diluted to 2× the final concentration in the above medium. Final drug concentrations ranged from 0.05 to 50 µM. After 24 hours at 37° C., 2.5 µCi of $^3$H-Thymidine (5 Ci/mmol) was added to each well. At 48 hours, the cells were harvested onto glass filters and radioactivity was measured with a scintillation counter.

The IC$_{50}$ value was determined as the concentration leading to a 50% reduction of $^3$H-thymidine incorporation relative to control wells. Each value shown in Table 1, above, resulted from 6 replicates for each compound.

The foregoing examples are illustrative of the present invention and are not intended to be construed as limiting thereof. The invention is defined by the following claims, with equivalents of the claims to be included therein.

That which is claimed is:

1. A method of treating *Cryptococcus neoformans* in a subject in need of such treatment, comprising administering to said subject a compound of Formula I-A:

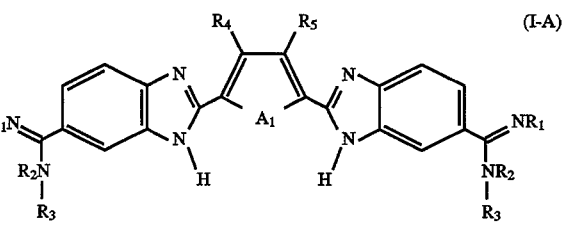

wherein:

R$_1$ and R$_2$ are each independently selected from the group consisting of H, lower alkyl, alkoxyalkyl, cycloalkyl, aryl, alkylaryl, hydroxyalkyl, aminoalkyl, or alkylaminoalkyl, or R$_1$ and R$_2$ together represent alkylene or R$_1$ and R$_2$ together are:

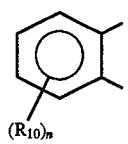

wherein n is a number from 1 to 3, and R$_{10}$ is H or —CONHR$_{11}$NR$_{15}$R$_{16}$ wherein R$_{11}$ is lower alkyl and R$_{15}$ and R$_{16}$ are each independently selected from the group consisting of H and lower alkyl; and $R_3$ is H, hydroxy, lower alkyl, cycloalkyl, aryl, alkylaryl, alkoxyalkyl, hydroxycycloalkyl, alkoxycycloalkoxy, hydroxyalkyl, aminoalkyl or alkylaminoalkyl;

$A_1$ is —N($R_{12}$)—;

wherein $R_{12}$ is hydrogen, lower alkyl, hydroxy, aminoalkyl or alkylaminoalkyl; and $R_4$ and $R_5$ are each independently selected from the group consisting of H, lower alkyl, halogen, aryl, arylalkyl, aminoalkyl, aminoaryl, oxyalkyl, oxyaryl, or oxyarylalkyl, or a physiologically acceptable salt thereof, in an amount effective to treat *Cryptococcus neoformans*.

2. The method according to claim 1, wherein said subject is afflicted with *Cryptococcus neoformans*.

3. The method according to claim 1, wherein said subject is at risk of developing *Cryptococcus neoformans* and said compound is administered in a prophylactically effective amount.

4. The method according to claim 1, wherein $R_1$ and $R_2$ together represent a $C_2$ to $C_4$ alkylene, and $R_3$ is H.

5. The method according to claim 4, wherein $R_1$ and $R_2$ together represent $C_2$ alkylene.

6. The method according to claim 4, wherein $R_1$ and $R_2$ together represent $C_3$ alkylene.

7. The method according to claim 1, wherein each of $R_1$, $R_2$ and $R_3$ is H.

8. The method according to claim 1, wherein each of $R_1$ and $R_3$ is H and $R_2$ is lower alkyl.

9. The method according to claim 1, wherein said compound is selected from the group consisting of:

2,5-bis(5-amidino-2-benzimidazolyl)pyrrole;

2,5-bis-[5-(2-imidazolinyl)-2-benzimidazolyl]pyrrole;

1-methyl-2,5-bis(5-amidino-2-benzimidazolyl)pyrrole;

1-methyl-2,5-bis[5-(2-imidazolyl)-2-benzimidazolyl] pyrrole and 1-methyl-2,5-bis[5-(1,4,5,6-tetrahydro-2-pyrimidinyl)-2-benzimidazolyl]pyrrole;

or a physiologically acceptable salt thereof.

* * * * *